United States Patent [19]

Balhorn

[11] 4,331,660
[45] May 25, 1982

[54] FISH EGG FUNGICIDE

[76] Inventor: Rodney L. Balhorn, P.O. Box 751, Livermore, Calif. 94550

[21] Appl. No.: 239,395

[22] Filed: Mar. 2, 1981

[51] Int. Cl.³ .............................................. A01N 59/16
[52] U.S. Cl. .................................................... 424/131
[58] Field of Search ........................................ 424/131

[56] References Cited

FOREIGN PATENT DOCUMENTS 1455861 10/1966 France .

OTHER PUBLICATIONS

The Merck Index, 9th Ed., (1976), p. 289.

*Primary Examiner*—Allen J. Robinson
*Attorney, Agent, or Firm*—Henry P. Sartorio

[57] ABSTRACT

The control of fungus is a serious problem in the hatching of fish. Sodium dichromate, potassium dichromate and chromium trioxide are effective fungicides for the inhibition of fungal growth on fish eggs and young fry during hatching.

5 Claims, No Drawings

FISH EGG FUNGICIDE

BACKGROUND OF THE INVENTION

The invention relates to fungicides and more particularly to fungicides for the inhibition of fungal growth on fish eggs and young fry during the hatching of fish.

A serious problem in commercial fish hatcheries and in the breeding of tropical and cold water fish by hobbyists is control of fungus. The eggs and young fry are very susceptible to fungus, including Saprolegnia, which very rapidly spreads from diseased eggs to healthy fertile eggs and developing embryos. Manual removal of diseased eggs is one method of fungal control but is difficult to perform. Treating eggs in sea water is another method but requires that the fish can survive in salt water and is usually only partly effective. The most common method is the use of antifungal chemicals or fungicides, the most common of which are methylene blue, malachite green, and acriflavin. These methods are frequently ineffective or only partially effective in preventing the growth of various types of fungus in fish eggs. Some chemicals, e.g., acriflavin, appear to induce sterility in the fish hatched from treated eggs.

It is an object of the invention to effectively prevent the growth of fungus on the eggs of a great variety of different fish.

It is another object to effectively kill the fungus without killing the eggs.

It is also an object to provide a method that is not toxic to the adult fish.

It is a further object to provide a method in which the adult fish obtained from treated eggs are fertile.

It is another object to provide a fungicide that is not toxic to aquarium plants and will not inhibit the growth of beneficial algae used by the fry as food.

It is also an object to provide a fungicide that is stable indefinitely and does not significantly alter the pH of the water at effective concentrations.

It is a further object of the invention to provide a fungicide that does not stain the glass or sealant of the aquarium and that may be used along with charcoal filtration.

SUMMARY OF THE INVENTION

The invention is a method of inhibiting the growth of fungus on fish eggs and young fry during hatching by adding to the hatching water a small but effective amount of a chromium compound selected from the group of sodium dichromate, potassium dichromate and chromium trioxide.

DETAILED DESCRIPTION OF THE PREFERRED EMBODIMENTS

The invention is a method of inhibiting the growth of fungus on fish eggs and young fry using a chromium compound selected from the group of sodium dichromate ($Na_2Cr_2O_7$), potassium dichromate ($K_2Cr_2O_7$) and chromium trioxide ($CrO_3$) as a fungicide. A small but effective amount, generally in the range of about 0.2 to about 0.5 g/gal, of the fungicide is added to the hatching water either in solid form or as a prepared concentrate at the time the eggs are produced. Additionally, 30–50% of the water can be changed each day after the fish have hatched to dilute out the fungicide.

Sodium dichromate, potassium dichromate and chromium trioxide are effective fungicides for fish eggs and young fry because they are relatively mild chemical oxidants, are soluble, are non-toxic, do not decompose, and do not produce developmental abnormalities. Table I shows the effects of the compounds according to the invention and other oxidants as fungal growth inhibitors. Ten infertile and ten fertile Branchydanio rerio eggs were incubated in aquarium water at 80° F. containing the specified compounds. The eggs were examined at 24-hour intervals, the number of fungused eggs or developing embryos were counted, and the results of several tests were averaged.

TABLE I

| Compound | Concentration (gm/gal) | Number Infertile Eggs Fungused | Number Fertile Eggs Hatched |
|---|---|---|---|
| Sodium dichromate | 0.21 | 0% | 100% |
| Potassium dichromate | 0.27 | 0% | 95% |
| Chromium trioxide | 0.34 | 0% | 90% |
|  | 0.10 | 100% | 100% |
| Sodium chromate | 0.17 | 90% | 100% |
| Potassium ferricyanide | 0.24 | 100% | 50% |
| Hydrogen peroxide | 0.01% | 100% | 0% |
| Sodium hypochlorite | 0.001% | 100% | 0% |
| Control | — | 100% | 95% |

The results show that the compounds according to the invention are highly effective in preventing the growth of fungus without killing the fertile eggs, most of which hatched. The chromium trioxide at too low a concentration is ineffective as a fungicide. All the other compounds, including chromates, are ineffective as fungicides. The chromates are too weak oxidants to be effective. The stronger oxidants, particularly hydrogen peroxide and sodium hydrochlorite, also kill the developing embryos.

The effective concentration of the chromium compounds according to the invention are shown in Table II. The fungicide was applied to spawns of P. scalare containing 200–400 eggs, and the eggs were incubated at 80° F. with aeration. The number of fungused eggs was determined after three days.

TABLE II

| Concentration (g/gal) | Percent Eggs Fungused |
|---|---|
| Control | 100% |
| 0.05 | 100% |
| 0.19 | 2–8% |
| 0.38 | 0% |

At concentrations below about 0.2 g/gal the fungicides are not entirely effective. An upper limit of about 0.5 g/gal is selected in order to not significantly alter the pH of the water, which is detrimental to the eggs and fish, and to keep the dosage well below concentrations that are toxic.

The chromium compounds according to the invention are effective as fungal growth inhibitors on a great variety of fish. The following are species upon which the fungicide was tested and found effective: angelfish (Pterophyllum scalare, var. silver, marble, gold, blushing, gold-blushing, half-black, Spanish lace, black-lace, and zebra veiltails), zebra danio (Brachydanio rerio), pearl danio (Brachydanio albolineatus), leopard danio (Brachydanio frankei), gold gouramis (Trichogaster trichopteris), banjo catfish (Bunocephalus coracoideus), killifish (Aphyosemion gardneri, yellow strain; A. australe, orange), discus (Symphysodon aequifasciata axelrodi cross with S. aequifasciata haraldi), Lamprologus brichardi, Lamprologus leleupi, Juliodochromis marleri, Corydoras aeneus, Iodotropheus sprengerae, Hyphessobrycon serpae, and Pseudotropheus zebra, tangerine. Conventional fungicides are ineffective upon several of these species, as shown in Table III for *P. scalare*. Twenty eggs were generally utilized per test, except that the methylene blue, acriflavin, and methylene blue plus malachite green were applied to spawns of 200-400 eggs.

TABLE III

| Fungicide | Concentration | Percent Eggs Fungused |
|---|---|---|
| Sodium Dichromate | 0.19 g/gal | 0% |
| Fungus Off | 1 drop/gal | 100% |
| Phenoxyethanol | 2 drops/gal | 100% |
| Methylene Blue, 1% | 1 drop/gal | 100% |
| P. permanganate (2 hr pretreatment) + Methylene Blue | 25 drops/gal | 70% |
| Methylene Blue, 1% | 50 drops/gal | 98% |
| Acriflavin | 3 drops/gal | 90% |
| Methylene Blue + Malachite Green (0.75%) | 3 drops/gal 1 drop/gal | 100% |
| Control | No additive | 100% |

In addition to being effective fungal growth inhibitors, the chromium compounds according to the invention have other advantageous properties as well. The fungicide is not toxic to adult fish. Angelfish, gold gouramis, pearl danios, *Betta splendens*, guppies, mollies, and killifish (*A. gaardneri* and *A. australe*) were exposed for up to one month. There were no mortalities and no detectable adverse effects. Since the fungicide does not appear to be toxic, it may also be effective to eradicate various types of fungal lesions on adult fish.

Adult fish or fish raised from eggs treated with the fungicide according to the invention are not sterilized by the treatment, but are fertile. Fish from five different species, *Julidochromis marlieri, Lamprologus brichardi, Aphyosemion gardneri, Iodotropheus sprengerae, Pterophyllum scalare* var. marble and gold veiltail, were hatched in fungicide at 0.38 g/gal concentration, raised to maturity and spawned, producing fertile eggs.

The fungicides are not toxic to aquarium plants, including Java moss (*Vesicularis dubyana*), water sprite (*Ceratopteris thalicroides*), duckweed (*Lemna sp.*), and various species of freshwater algae. This is important since eggs are often spawned in or upon plants and must be treated there. The fungicide does not inhibit the growth of beneficial algae which are used as food by the fry. The compounds are not bound by charcoal and removed from the water so they can be used along with charcoal filtration in an aquarium. The fungicides also do not stain the glass or silastic sealant used in aquariums.

Changes and modifications in the specifically described embodiments can be carried out without departing from the scope of the invention which is intended to be limited only by the scope of the appended claims.

I claim:

1. A method for inhibiting the growth of fungus on fish eggs and young fry in hatching water during the hatching of fish, comprising adding a fungicidally effective amount of a chromium compound selected from the group consisting of sodium dichromate, potassium dichromate and chromium trioxide to the hatching water in a concentration in the range of about 0.2 to about 0.5 g/gal.

2. The method of claim 1 wherein the compound is added to the water as a solid.

3. The method of claim 1 wherein the compound is added to the water as a prepared concentrate.

4. The method of claim 1 wherein the compound is added to the water when the eggs are first spawned.

5. The method of claim 1 further including the step of changing 30-50% of the water on the day of hatching and on each succeeding day.

* * * * *